United States Patent [19]

Bezman

[11] 4,352,945

[45] Oct. 5, 1982

[54] DIISOPROPYL ETHER REVERSION IN ISOPROPANOL PRODUCTION

[75] Inventor: Susan A. Bezman, Point Richmond, Calif.

[73] Assignee: Chevron Research Company, San Francisco, Calif.

[21] Appl. No.: 316,579

[22] Filed: Oct. 30, 1981

[51] Int. Cl.³ .............................................. C07C 29/04
[52] U.S. Cl. ..................................................... 568/899
[58] Field of Search ......................................... 568/899

[56] References Cited

U.S. PATENT DOCUMENTS

| 2,519,061 | 8/1950 | Mason | 568/907 |
|---|---|---|---|
| 2,648,711 | 8/1953 | Carrier | 568/899 |
| 2,813,908 | 11/1957 | Young | 568/899 |
| 2,818,439 | 12/1957 | Hakala et al. | 568/899 |
| 3,170,000 | 2/1965 | Verdol | 568/907 |

Primary Examiner—Joseph E. Evans
Attorney, Agent, or Firm—D. A. Newell; S. R. La Paglia; S. H. Roth

[57] ABSTRACT

A process for the production of isopropanol by the hydration of propylene in which the by-product diisopropyl ether is subjected to a reversion reaction and the resulting propylene is recycled to the hydration stage.

9 Claims, 1 Drawing Figure

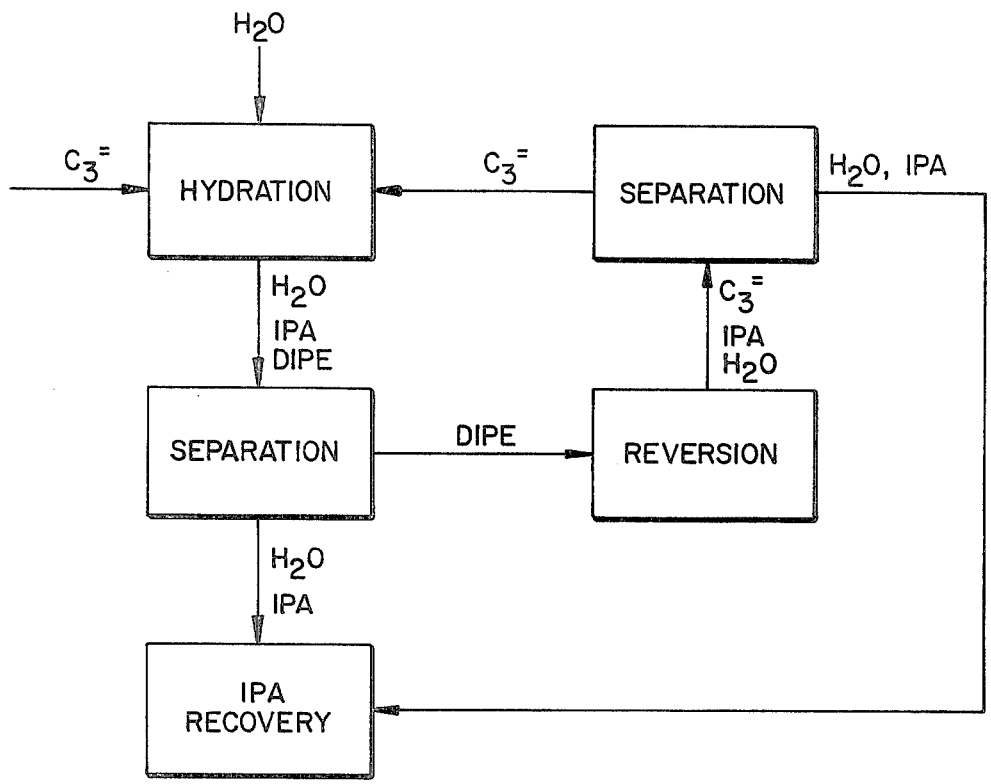

DIISOPROPYL ETHER REVERSION IN ISOPROPANOL PRODUCTION

BACKGROUND OF THE INVENTION

The present invention relates to a process for the hydration of olefins. Specifically, the invention relates to a process for the hydration of propylene to produce isopropanol for blending into gasoline.

As is well known, alkylation can produce a premium grade gasoline component from olefins by reaction with isoparaffins such as isobutane or isopentane. Refineries have, however, experienced a shortage of isoparaffins, particularly isobutane, and therefore have an excess of olefins. So a way to place these olefins into the motor gasoline pool is needed. At the same time, gasoline octane requirements have increased and the use of traditional lead-containing gasoline additives has been largely discontinued. It has, therefore, become necessary to find alternative means to produce high octane fuel compositions without the necessity for alkylation. This may be accomplished by producing oxygenated compounds, e.g., isopropanol from the excess olefins.

Furthermore, some gasolines have a maldistribution of high octane components and when used without fuel injection can knock under driving conditions not predicted by model octane testing. Addition of isopropanol to such gasolines provides a good way to improve octane component distribution.

Isopropanol may be made with very high propylene conversions per pass using even dilute $C_3$ olefin-containing feedstocks at low space velocities. Under these conditions, however, especially at low water to olefin molar feed ratios, large amounts of diisopropyl ether (DIPE) may be formed. The present process relates particularly to the treatment of the DIPE by-product so that the isopropanol production process can be conducted more efficiently.

BRIEF DESCRIPTION OF THE DRAWING

The sole FIGURE is a schematic representation of a process in accordance with the invention.

SUMMARY OF THE INVENTION

The present invention relates to a process for producing isopropanol comprising the steps of contacting water and a propylene-containing feedstock in a hydration reaction zone with a hydration catalyst to produce isopropanol and by-product diisopropyl ether, separating the diisopropyl ether and contacting it with a reversion catalyst under reversion conditions to produce an effluent from which propylene is recovered and recycled to the hydration reaction zone.

DESCRIPTION OF THE PREFERRED EMBODIMENTS

The process of the present invention enables one to use excess $C_3$ olefins and incorporate them as high octane components into the motor gasoline pool without alkylation. In addition, the present process provides a method for employing the by-product of the propylene hydration reaction whereby this by-product is in effect incorporated into the motor gasoline pool.

The present invention is most advantageously employed in a process for producing isopropanol by the hydration of propylene. Although any such process may be employed, the preferred method is the one disclosed in my co-pending U.S. patent application Ser. No. 277,438, filed June 25, 1981 which is incorporated by reference herein. In that method, a feedstock comprising $C_3$ hydrocarbons having a propylene content of from about 60% to about 85% is used. Preferred is a feed such as that which could be obtained by distilling off a $C_3$ cut from a fluid catalytic cracker. It is possible by using the combination of reaction conditions described below to obtain a high conversion per pass even employing such dilute feedstocks.

The feedstock containing propylene is reacted with water in the presence of an ion exchange catalyst. The catalyst is preferably a sulfonated macroreticular copolymer of styrene and divinylbenzene in the acid form. Catalysts modified by chlorination to withstand higher temperatures, such as Amberlyst XN 1011 and Amberlite XE 372, manufactured by Rohm and Haas, are particularly preferred. Other catalysts suitable for the hydration of propylene and methods for their preparation are described in U.S. Pat. No. 2,813,908, incorporated by reference herein.

In propylene hydration, a propylene-containing feedstock is generally mixed with water in a ratio of water to propylene from about 5 to 15, preferably from about 8 to 12 and most preferably about 8. The mixture is then fed to a reactor, preferably in a downflow, trickle bed configuration, to contact the catalyst.

Hydration conditions generally include a pressure of from about 1,000 to 2,000, preferably 1,400 to 1,500 psig and a temperature of from about 275° to 375° F., preferably from about 290° to 355° F. The conditions are selected so that the propylene is in a super-critical gas phase and the water is primarily in the liquid phase. Finally, the propylene liquid hourly space velocity is from about 0.15 to about 1.5 per hour, preferably from about 0.4 to 0.5 per hour.

In the hydration stage, the percent propylene conversion should be maintained at a predetermined level, generally from about 50% to 90%, preferably about 67%. To do so, the temperature in the reactor can be raised incrementally to compensate for the loss of catalyst activity during the course of the reaction.

The crude product which emerges from the bottom of the reactor generally contains water, isopropanol, diisopropyl ether (a by-product), propylene, propane, any $C_4$ hydrocarbons present in the feed, traces of alcohols or ethers derived from reactions of $C_4$ hydrocarbons and traces of $C_6$ hydrocarbons formed by dimerization of propylene. This crude product may be passed through one or more conventional gas-liquid separators to separate the gases, i.e., propane, unreacted propylene and trace $C_4$ and lower hydrocarbons from the liquids, i.e., isopropanol, water and diisopropyl ether.

The separated gases generally contain at least 30% unreacted $C_3$ olefins. Such olefins, of course, may be fed to a conventional alkylation plant where they are allowed to react with isoparaffins in the presence of a suitable catalyst such as HF or sulfuric acid. The resultant alkylation product, presumably a mixture of high-branched $C_7$ paraffins is a high octane product suitable for direct addition to the motor gasoline pool. As discussed, the desirability of alkylation is limited by the shortage and high expense of the requisite isobutane.

Propylene obtained from the overhead of the liquid-gas separator may be catalytically oligomerized to make olefinic gasoline, a high octane gasoline pool component as disclosed in my co-pending U.S. patent application Ser. No. 277,437, filed June 25, 1981. Such oligomerization obviates the need to alkylate excess olefins, significantly reducing the process cost.

The crude liquid product from hydration which contains water, isopropanol, diisopropyl ether and perhaps traces of $C_4$ olefin-derived ethers and/or alcohols and $C_6$ olefins is generally caustic neutralized or acid is removed by ion exchange. This product is passed to a first distillation column which is generally operated at near atmospheric pressure at a temperature so that the product taken overhead is primarily diisopropyl ether (actually the low-boiling azeotrope which also contains 4% isopropanol and 5% water, b.p. 62° C.). The bottoms from this first distillation column, containing primarily isopropanol and water, are passed through a second distillation column. The overhead from the first column, primarily diisopropyl ether, is treated in accordance with the present invention as discussed hereinbelow.

The second distillation column containing the isopropanol and water, is operated generally at or near atmospheric pressure and at a temperature such that the isopropanol-water azeotrope (b.p. 80° C.) having the composition of 87.8 weight percent isopropanol and 12.2 weight percent water is taken overhead. The column bottoms which consist primarily of a very dilute aqueous salt solution may be either (a) desalted by treatment with an ion exchange resin and the pure water recycled with makeup water to the hydration reactor or (b) discarded.

Isopropanol is typically separated from the isopropanol-water azeotrope so it can be blended with a gasoline blending hydrocarbon stream resulting in a oxygenated fuel-containing blending stock which can be used directly in the motor gasoline pool. Such separation may be accomplished by any of the conventional extraction and/or azeotropic distillation techniques. The preferred method which provides a simple, economical way to introduce isopropanol from an isopropanol-water azeotrope directly into a gasoline blending stock, an extractive blending technique, is the subject of my co-pending U.S. patent applications Ser. Nos. 277,295, 277,296 and 277,440, all filed June 25, 1981 and which are incorporated by reference herein.

Briefly, in accordance with those methods, the azeotrope is dehydrated by combining it with a gasoline blending hydrocarbon stream. The gasoline blending hydrocarbon may be any hydrocarbon that can be added to the motor gasoline pool, including straight run, alkylate, FCC gasoline, reformate, or their mixtures such as Chevron Unleaded Regular gasoline (ULR). The hydrocarbon may also comprise middle distillates such as hydrocarbon mixtures boiling in the jet or diesel fuel range. The mixing may be done in a mixing tank, but is preferably accomplished by use of inline mixers such as the pipe mixers manufactured by Komax Systems, Inc., as opposed to the energy intensive extractors. From about 2 to 15 volumes of hydrocarbon per volume of azeotrope, preferably at least 10 volumes are employed. A milky emulsion forms on mixing. This emulsion is separated rapidly into two phases for example by passing it through a commercial water filter coalescer.

For a 10:1 volume ratio, regardless of the rate of separation, the hydrocarbon layer composition is about 91.2 weight percent gasoline, 8.3 weight percent isopropanol and 0.41 weight percent water. The aqueous phase consists essentially of about 75% water and 25% isopropanol. This layer represents only a small volume of material, however, (less than 0.1) and may be recycled to the second distillation column. The isopropanol-hydrocarbon phase emerging from the coalescer can be blended with additional gasoline or used directly as automotive fuel without further treatment.

In accordance with the invention, the overhead from the first distillation column which is primarily diisopropyl ether (and about 4% IPA and 5% water), which was divided from the effluent from the hydration zone is contacted with a reversion catalyst in a second reaction zone under reversion conditions.

Almost any acid catalyst may be suitably used as the reversion catalyst in accordance with the present invention. Nearly quantitative (>95%) reversions to propylene and water were obtained at 50 psig and 330° F. with Amberlite XE 372, the preferred catalyst for the propylene hydration reaction. Silicalite, an essentially alumina free intermediate pore size zeolite of the ZSM-5-type as disclosed in U.S. Pat. No. 4,061,724, incorporated by reference, is also useful as a reversion catalyst although use of such catalyst requires a higher temperature.

Special zeolitic catalysts are not required to achieve high degrees of conversion. Nearly quantitative conversion of DIPE to propylene was obtained using a silica-alumina cogel catalyst at 515° F., but no conversion was obtained at moderate temperatures employing this catalyst (343° F.). In fact, alumina itself reverted greater than 99% of DIPE to propylene at 520° F. and 50 psig. Thus, in accordance with the present invention the reversion catalyst may comprise any acid catalyst, preferably an acid ion exchange resin, a silica-alumina cogel, alumina, aluminosilicates and zeolites including the ZSM-5 type zeolites. Alumina is most preferred.

The reversion conditions will depend in part on the acidity of the reversion catalyst. Generally, a catalyst having low acidity requires a higher temperature than one having a higher acidity. For example, with Amberlite XE 372, 99% conversion was obtained at a temperature of 330° F., whereas silicalite converted only 18% of the DIPE to propylene at 343° F. and 99% conversion to propylene was obtained only at about 525° F. Reversion temperatures will generally be from about 250° to 550° F.

Regardless of the particular catalyst, reversion conditions will include a low pressure, generally from atmospheric to about 500 psig and preferably from atmospheric to about 200 psig. The liquid hourly space velocity is generally from about 0.1 to 10 and preferably from about 0.5 to 5.

The effluent from the reversion zone will comprise propylene, IPA and water. This effluent is then passed to a separation zone, e.g., a gas-liquid separator. The separated propylene is recycled to the hydration reaction zone in accordance with the invention. The liquid stream comprising IPA and water may be passed to an IPA recovery zone.

The following examples are merely illustrative and are not intended to constitute a limitation on the invention which is defined by the appended claims.

EXAMPLES

The following Table I set forth the results of tests which illustrate the concept of the present invention. All the runs were carried out in a ⅜" O.D. Teflon-lined 316 SS reactor tube into the midsection of which the indicated catalyst charge was loaded. Two beds of 20 to 32 mesh alundum particles which were each about 5"

long were placed in the reactor tube to provide for mixing of the reagents and supporting the catalyst charge, respectively.

The feed, 95.6% DIPE and 4.4% IPA, simulates the organic composition of an upper layer of decanted DIPE/IPA/H$_2$O azeotrope which would be obtained from the overhead of the first distillation column. (Run No. 4 employed an organic feed composition 96.5% DIPE and 3.5% IPA.) The feed was passed into the reactor tube from the top at the indicated space velocities. The LHSV for water was zero in all cases except Run No. 4 where it was 0.01 hr$^{-1}$.

Because of the multicomponent nature of both product and feed, the results in Table I are expressed not in terms of conversion and selectivity, but rather in terms of the potential propylene content of each component, normalized so that the total C$_3$= content of the feed and product is 100% (e.g., 1 mole of DIPE contains 2 equivalents of C$_3$=; 1 mole of IPA contains 1 equivalent of C$_3$=).

The catalyst designations are as follows: "Silicalite" signifies Linde Silicalite obtained from Union Carbide; "Cogel" signifies a 65% alumina-35% silica cogel; "Alumina" signifies alumina; and "XE 372" signifies Amberlite XE 372.

TABLE I

| | Run | | | | | | |
|---|---|---|---|---|---|---|---|
| | 1 | 2 | 3 | 4 | 5 | 6 | 7 |
| Catalyst | XE 372 | XE 372 | Silicalite | Silicalite | Cogel | Cogel | Alumina |
| Temperature, °F. | 330 | 330 | 343 | 525 | 508–521 | 340–347 | 520 |
| Pressure, psig | 50 | 500 | 50 | 50 | 50 | 50 | 50 |
| Organic LHSV, hr$^{-1}$ | 0.95 | 0.95 | 0.94 | 0.93 | 1.2 | 1.2 | 0.83 |
| % C$_3$= Equivalents In Product | | | | | | | |
| DIPE | 0.5 | <18 | 77 | 0.1 | 0.02 | 94 | 0.3 |
| IPA | 0.4 | 16 | 5 | 0.5 | 0.3 | 4 | 0.3 |
| C$_3$= | 99 | 36 | 18 | 96.8 | 99 | 2 | 99 |
| Mogas | — | — | — | 2.6 | 1 | — | — |

Although the present invention has been illustrated by reference to specific embodiments, it will be apparent to those skilled in the art that various changes and modifications may be made which clearly fall within the scope of this invention. It is not the intent of applicant to be bound by the specific embodiments described, but rather only by the appended claims.

I claim:

1. A process for producing isopropanol comprising:
   (a) contacting water and a feedstock comprising propylene with a catalyst comprising an acid ion exchange resin in a first reaction zone under hydration conditions to produce a first stream;
   (b) dividing the first stream into a second stream comprising water and isopropanol and a third stream comprising diisopropyl ether;
   (c) contacting the third stream with a reversion catalyst in a second reaction zone under reversion conditions to produce a fourth stream;
   (d) separating propylene from the fourth stream;
   (e) recycling the propylene to step (a); and
   (f) recovering isopropanol from the second stream.

2. The process of claim 1, wherein the hydration conditions include a temperature of from about 275° to 375° F., a pressure of from about 1,000 to 2,000 psig, a water to propylene molar ratio of from about 5 to 15 and a propylene liquid hourly space velocity of from about 0.15 to 1.5.

3. The process of claim 1, wherein the feedstock comprises C$_3$ hydrocarbons of which from about 60 to 85% are propylene.

4. The process of claim 1, wherein the acid ion exchange resin is a sulfonated macroreticular copolymer of styrene and divinylbenzene.

5. The process of claim 4, wherein the acid ion exchange resin is in a chlorinated form.

6. The process of claim 1, wherein the reversion catalyst comprises a silica-alumina cogel.

7. The process of claim 1, wherein the reversion catalyst comprises alumina.

8. The process of claim 1, wherein the reversion catalyst comprises a zeolitic crystalline aluminosilicate.

9. The process of claim 1, wherein the reversion catalyst comprises an essentially alumina free intermediate pore size zeolite.

* * * * *